United States Patent [19]

Genese

[11] 4,192,306
[45] Mar. 11, 1980

[54] CATHETER PLACEMENT ASSEMBLY HAVING AXIAL AND ROTATIONAL ALIGNMENT MEANS

[75] Inventor: Joseph N. Genese, Waukegan, Ill.

[73] Assignee: Abbott Laboratories, North Chicago, Ill.

[21] Appl. No.: 935,442

[22] Filed: Aug. 21, 1978

[51] Int. Cl.² ............................................. A61M 5/00
[52] U.S. Cl. ............................ 128/214.4; 128/214.2; 128/348; 128/349 R; 128/DIG. 16
[58] Field of Search ............. 128/214.4, 214.2, 214 R, 128/348, DIG. 16, 349, 221

[56] References Cited

U.S. PATENT DOCUMENTS

| Re. 27,797 | 10/1973 | Sorenson et al. | 128/214.4 |
|---|---|---|---|
| 3,589,361 | 6/1971 | Loper | 128/214.4 |
| 3,720,210 | 3/1973 | Diettrich | 128/214.4 |
| 3,769,975 | 11/1973 | Nimoy et al. | 128/214.4 |
| 3,782,383 | 1/1974 | Thompson | 128/214 R |
| 3,809,081 | 5/1974 | Loveless | 128/214.4 |
| 3,867,937 | 2/1975 | Schwartz | 128/214.4 |
| 3,906,946 | 9/1975 | Nordström | 128/214.4 |
| 4,068,659 | 1/1978 | Moorehead | 128/214.4 |
| 4,106,506 | 8/1978 | Koehn et al. | 128/214.4 |
| 4,129,128 | 12/1978 | McFarlane | 128/214 R |

*Primary Examiner*—Henry K. Artis
*Attorney, Agent, or Firm*—Robert L. Niblack; Aaron L. Hardt; Robert S. Beiser

[57] ABSTRACT

A needle-inside, catheter placement assembly including a spliced, two-part needle and a catheter unit comprising a catheter, winged catheter insertion means, flexible tubing and tube hub, wherein axial and rotational alignment of the needle and catheter unit are maintained by mechanically interlocked complementary portions of the needle and lumen of the winged catheter insertion means.

12 Claims, 12 Drawing Figures

CATHETER PLACEMENT ASSEMBLY HAVING AXIAL AND ROTATIONAL ALIGNMENT MEANS

BACKGROUND OF THE INVENTION

The present invention relates to intravenous catheter placement assemblies and, more particularly, to needle-inside, catheter placement assemblies having axial and rotational alignment means.

Catheter placement assemblies of the needle-inside type are well known in the prior art. U.S. Pat. No. 3,312,200 granted to M. Eisenberg on Apr. 4, 1967 discloses such a catheter placement assembly. U.S. Pat. No. 3,809,081 granted to J. Loveless on May 7, 1974 discloses such a catheter placement assembly having an obturator threadably connected to the catheter hub. U.S. Pat. No. 3,589,361 granted to D. Loper on June 10, 1968 discloses such a catheter placement assembly having axially movable winged insertion means disposed on the catheter. U.S. Pat. No. 3,769,975 granted to M. Nimoy, et al. on Nov. 6, 1973 discloses such a catheter placement assembly having a catheter unit comprising a catheter, winged catheter insertion means, flexible tubing and a tube hub.

An advantage of the Nimoy catheter placement assembly is that its tube hub is substantially spaced from the venipuncture site, thereby allowing the catheter to be securely attached to the patient at that site and allowing possible infection causing connections to an intravenous solution set to be made remote from the wound.

A major disadvantage of the Nimoy assembly is that axial and rotational alignment of the needle and catheter unit is difficult to maintain both prior to and during placement of the catheter into a patient. Nimoy attempts to solve this problem by the use of a removable plastic sleeve removably mounted on the flexible tubing. Loper discloses that flexing of his winged insertion means grasps both the catheter and needle during venipuncture. U.S. Pat. No. 3,537,451 granted to D. Beck, et al. on Nov. 3, 1970 discloses still another winged catheter insertion means which grasps both the catheter and their two-diametered needle during venipuncture.

Unfortunately, these prior art assemblies do not maintain axial or rotational alignment of the needle and catheter unit prior to placement of the catheter into the patient. Thus, proper axial or rotational alignment of the needle and catheter must be made by the user of the assembly just prior to venipuncture. Accordingly, it will be apparent that such a catheter placement assembly providing axial and rotational alignment of the needle and catheter unit thereof at all times would be advantageous and desirable.

SUMMARY OF THE INVENTION

Therefore, it is the primary object of this invention to provide a needle-inside, catheter placement assembly wherein the needle and catheter unit thereof are maintained in axial and rotational alignment at all times during their assemblage.

In accordance with these and other objects, there is provided by the present invention a needle-inside, catheter placement assembly having a spliced, two-part needle mechanically interlocked with complementary portions of the catheter unit thereof to maintain their axial and rotational alignment at all times during their assemblage.

BRIEF DESCRIPTION OF THE INVENTION

Other objects and attendant advantages will be obvious to those skilled in the art by reading the following detailed description in connection with the accompanying drawing wherein like reference characters designate like or corresponding parts throughout the several figures thereof and wherein:

FIG. 1 is a perspective view of a preferred embodiment of the needle-inside, catheter placement assembly of the present invention, FIG. 2 is an exploded view of the asembly of FIG. 1 showing the catheter unit and the needle thereof, FIG. 3 is a cross-sectional view of a portion of the assembly of FIG. 1, FIG. 4 is a cross-sectional view along the line 4—4 in FIG. 3 of the assembly thereof, FIG. 5 is an enlargement of a portion of FIG. 3, FIG. 6 is another embodiment of the needle of the present invention, FIG. 7 is a cross-sectional view of the needle of FIG. 6 incorporated into a catheter placement assembly viewed similarly as in FIG. 4, FIG. 8 is a cross-sectional view along the line 8—8 in FIG. 7 of the assembly thereof, FIGS. 9–11 are further embodiments of the needle of the present invention, and FIG. 12 is a cross-sectional view of the needle of FIG. 9 incorporated into a catheter assembly viewed similarly as in FIG. 8.

DETAILED DESCRIPTION OF THE INVENTION

Figure 1:
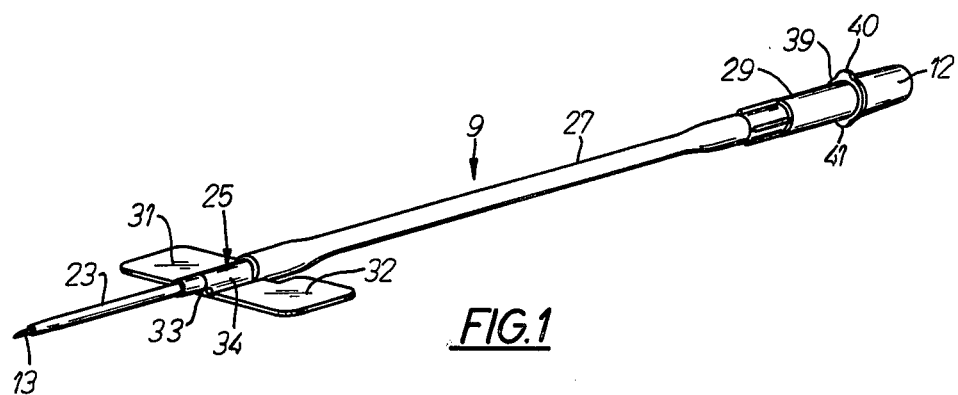

Referring to the drawing, there is shown in FIG. 1 a preferred embodiment of the needle-inside, catheter placement assembly 9 of this invention. Catheter placement assembly 9 comprises a needle 11 having its proximal end attached to a needle hub 12 and a beveled, sharpened distal end 13.

Figure 2:
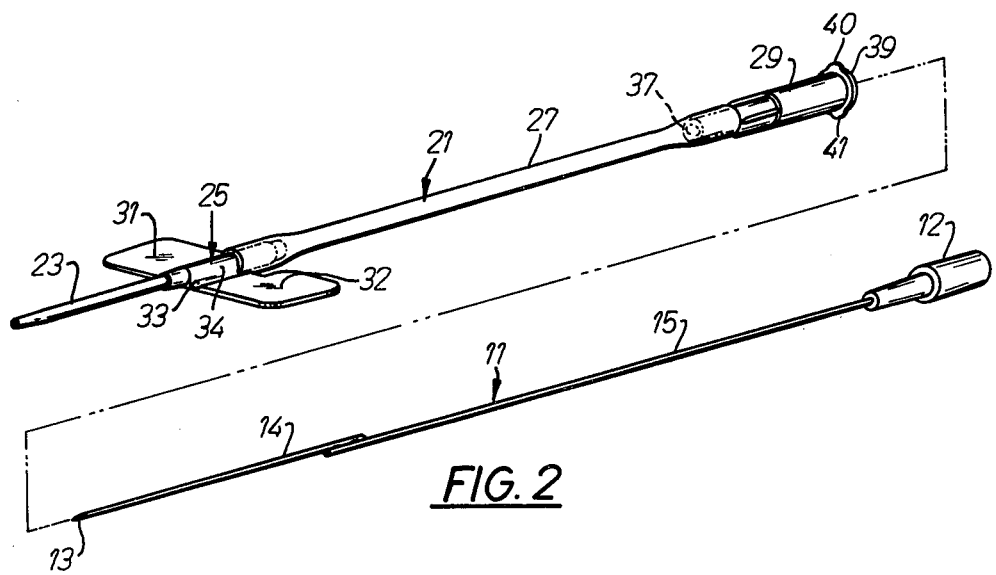
Figure 3:
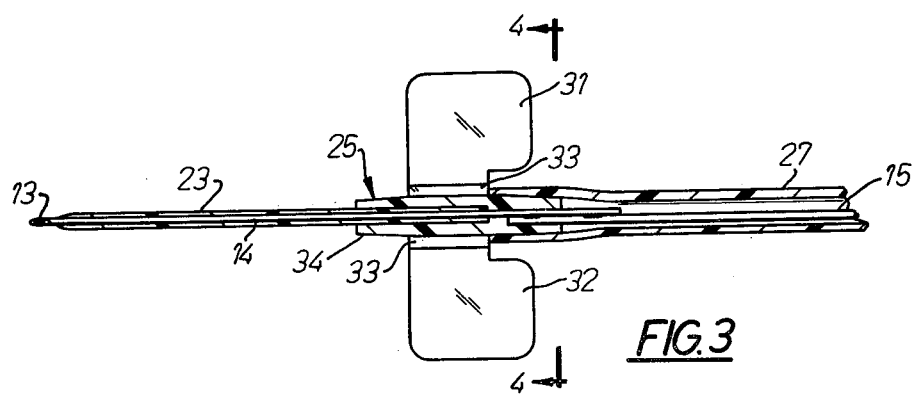
Figure 4:
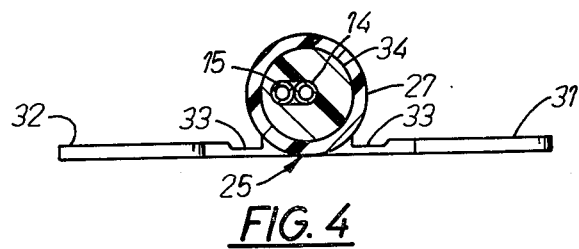

As shown in FIG. 2, needle 11 has a first portion 14 extending a predetermined distance from distal end 13 towards and joined to a second portion 15 which extends to the proximal end of needle 11. The distal portion of second portion 15 is in juxtaposition with the proximal portion of first portion 14. Preferably, first portion 14 is made of hollow, open-ended, stainless steel tubing, while second portion 15 can be a rod or tube of any material that will allow first portion 14 to be suitably attached thereto, e.g., by bonding, soldering, or welding. Advantageously, juxtaposed first and second portions 14, 15 provide a nonsymmetrical feature by which needle 11 can be mechanically locked in catheter placement assembly 9.

Figure 6:
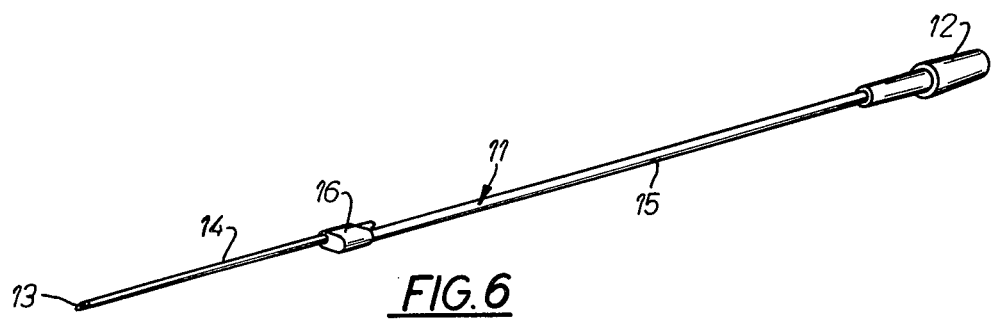
Figure 7:
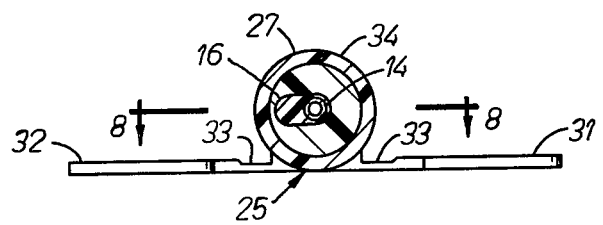
Figure 9:
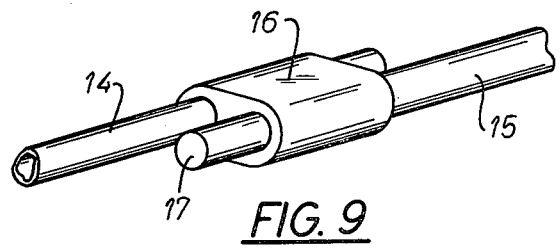
Figure 10:
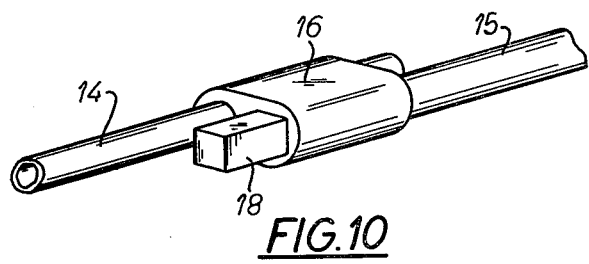
Figure 11:
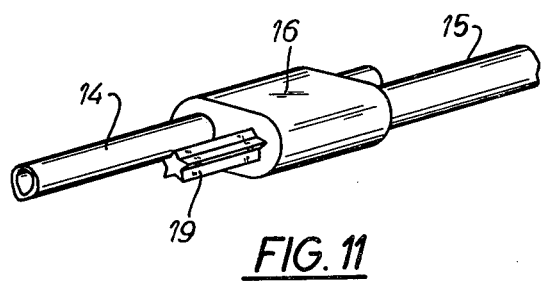

As seen in FIG. 6, needle 11 can also have its first and second portions joined or captured in juxtaposition by a joint 16. The distal end of second portion 15 can be encapsulated within joint 16 as shown, or it may extend from the distal end of joint 16, if so desired. Optionally, as shown in FIGS. 9–11, joint 16 can have projections 17, 18, 19 of various configurations projecting from its distal end. Joint 16 can be made of metal or plastics such as polyvinylchloride, polypropylene, or polyurethane.

Joint 16 can mechanically capture first and second portions 14, 15 or they can be bonded to joint 16. Alternatively, joint 16 can be insert molded around first and second portions 14, 15. Likewise, second portion 15 can be molded as a unitary extension of a molded joint 16, if so desired.

Catheter placement assembly 9 further comprises a catheter unit 21 having a flexible plastic catheter 23, winged catheter insertion means 25, flexible tubing 27 and tube hub 29. Catheter 23 is distally tapered at its distal end and can be made of any biocompatible flexible plastic material such as polyethylene, polypropylene, polytetrafluoroethylene or polyvinylchloride. The inner diameter of catheter 23 is substantially identical to the outer diameter of first portion 14 of needle 11.

Winged catheter insertion means 25 has a pair of flexible wings 31, 32 which, preferably, have a weakened portion or groove 33 adjacent a tubular portion 34 which has a lumen therethrough. Preferably, winged catheter insertion means 25 can be made of polyvinylchloride, but any other material that will enable wings 31, 32 to be flexed outwardly for aiding in the insertion of catheter 23 into the patient and subsequently downwardly, if necessary, for taping to the patient's body can be used.

The proximal end of catheter 23 is in fluid communication with the distal end of the lumen of tubular portion 34. As shown in FIG. 1, catheter 23 has an outer diameter substantially equal to the inner diameter of the lumen of tubular portion 34 and is inserted therein. However, it will be readily apparent that tubular portion 34 can be designed to receive catheter 23 on its outer diameter, if so desired.

The distal end of flexible tubing 27 is in fluid communication with the lumen of tubular portion 34 at its proximal end. As shown in FIG. 1, tubular portion 34 is inserted into flexible tubing 27, but it will be readily apparent that flexible tubing 27 can be inserted into tubular portion 34, if so desired. Preferably, flexible tubing 27 can be made of clear polyvinylchloride or polyurethane and has an inner diameter greater than the inner diameter of catheter 23.

The proximal end of flexible tubing 27 is connected in fluid communication to tube hub 29 which has a lumen 37 therethrough. Tube hub 29 is, preferably, made of polyvinylchloride, ABS copolymers or polycarbonate and, preferably, has a recess or female luer adapter at its proximal end. A collar 39 having ears 40, 41 extends outwardly from the proximal endwall of tube hub 29.

Figure 5:
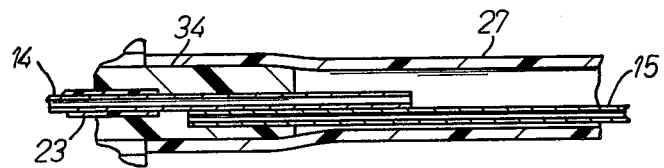
Figure 8:
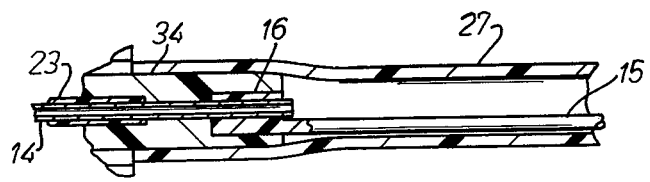
Figure 12:
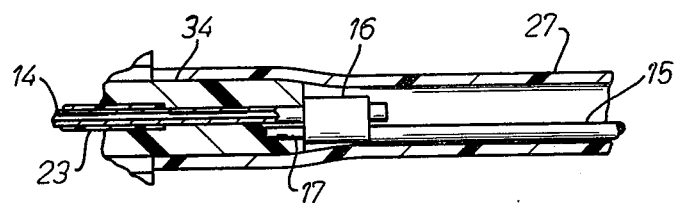

As best seen in FIGS. 5, 8 and 12, the lumen of tubular portion 34 of winged catheter insertion means 25 provides means complementary to the juxtaposed first and second portions 14, 15 of needle 11 by which catheter unit 21 and needle 11 can be mechanically interlocked in axial and rotational alignment at all times while assembled. As seen in FIG. 5, the lumen of tubular portion 34 is enlarged to a figure 8 at its proximal end to form a recess complementary to the distal end of second portion 15 of needle 11. Alternatively, as seen in FIG. 8, the proximal end of the lumen of tubular portion 34 can be enlarged to receive the entire joint 16, where needle 11 has such a joint, or as seen in FIG. 12, the lumen of tubular portion 34 can receive first portion 14 of needle 11, while an associated aperture at the proximal end of tubular portion 34 receives a projection 17 of joint 16.

On assembly, needle 11 is inserted into catheter unit 21 until the complementary means associated with the lumen of tubular portion 34 and the juxtaposed first and second portions 14, 15 of needle 11 meet and mechanically interlock. When that mechanical interlock has been achieved, the bevel at distal end 13 of needle 11 will be facing upwardly and projecting from the distal end of catheter 23 a chosen predetermined distance and the distal end of needle hub 12 will be situated within the lumen of tube hub 29. Preferably, the proximal end of first portion 14 of needle 11 will be situated within flexible tubing 27. The mechanical interlock will also prevent further distal movement of needle 11 with respect to catheter unit 21. Rotational misalignment or rotational movement of needle 11 with respect to catheter unit 21 is likewise prevented.

In use, it is anticipated that the catheter placement assembly 9 will be inserted into a patient by pinching flexible wings 31, 32 together to provide a finger grip and inserting the distal end of needle 11 and catheter 23 into the patient's vein in accordance with conventional venipuncture techniques well known in the medical practice. After the vein has been entered, if first portion 14 of needle 11 is hollow, it will allow blood to flow, or flashback, to flexible tubing 27 where it will readily be visible to indicate that the vein has been entered.

After the venipuncture has been achieved, the person inserting the assembly into the patient continues to grip wings 31, 32 in one hand and uses the other hand to disconnect needle hub 12 from the tube hub 29. Needle 11 is then withdrawn from catheter unit 21 and discarded. Catheter 23 if fully inserted into the vein, wings 31, 32 are then taped to the patient, a safety loop formed with flexible tubing 27 and an intravenous solution set attached to tube hub 29 in accordance with conventional techniques of the medical practice.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

I claim:

1. In an intraveneous catheter assembly including
   (1) a catheter unit comprising:
      (a) a flexible plastic catheter having a distally tapered distal end,
      (b) a winged catheter insertion means having a lumen therethrough, the proximal end of said catheter in communication with said lumen of said catheter insertion means via its distal end,
      (c) a flexible tubing having its distal end in communication with said lumen of said catheter insertion means via its proximal end,
      (d) a tube hub having a lumen therethrough, the proximal end of said flexible tubing in communication with said lumen of said tube hub via its distal end, and
   (2) a needle inserted through said catheter, winged catheter insertion means, flexible tubing and tube hub, said needle having a sharpened distal end extending beyond said distal end of said catheter and a proximal end attached to a needle hub; the improvement which comprises:
   complementary means associated with said lumen of said winged catheter insertion means and said needle mechanically interlocked to provide axial and rotational alignment of said needle relative to said catheter unit at all times, wherein said needle comprises a first portion extending a predetermined distance from said distal end toward said proximal end and spliced to a second portion in juxtaposition to said first portion, which second portion extends to said proximal end of said needle.

2. The intravenous catheter assembly defined in claim 1, wherein said first portion of said needle is a hollow tube open at both ends.

3. The intravenous catheter assembly defined in claim 2, wherein the proximal end of said first portion of said needle is disposed inside said flexible tubing.

4. The intravenous catheter assembly defined in claim 1, wherein said second portion of said needle is made of a solid rod.

5. The intravenous catheter assembly defined in claim 1, wherein said second portion of said needle is made of a tube.

6. The intravenous catheter assembly defined in claim 1, wherein said first portion is bonded directly to said second portion.

7. The intravenous catheter assembly defined in claim 1, wherein said first portion is joined to said second portion by a joint.

8. The intravenous catheter assembly defined in claim 7, wherein said second portion of said needle is molded as a unitary extension of said joint.

9. The intravenous catheter assembly defined in claim 1, wherein said proximal end of said winged catheter insertion means has an internal recess adjacent said lumen complementary to said second portion of said needle.

10. The intravenous catheter assembly defined in claim 9, wherein said lumen and said internal recess adjacent thereto intersect the proximal end of said winged insertion means in substantially the shape of a figure 8.

11. The intravenous catheter assembly defined in claim 7, wherein said proximal end of said winged catheter insertion means has an internal recess adjacent said lumen complementary to said joint joining said first and second portions of said needle.

12. The intravenous catheter assembly defined in claim 7, wherein said proximal end of said winged catheter insertion means has an aperture spaced from said lumen of said catheter insertion means complementary to a projection from the distal end of said joint joining said first and second portions of said needle.

* * * * *